United States Patent [19]

Balde et al.

[11] Patent Number: 4,528,026

[45] Date of Patent: Jul. 9, 1985

[54] 2-(OR4-)AMINO-5-ALKYLTHIO-PYRIMIDINE HERBICIDES

[75] Inventors: Daniel Balde, Paris; Gerard E. M. Boutemy, Milly La Foret, both of France

[73] Assignee: Produits Chimiques Ugine Kuhlmann, Paris, France

[21] Appl. No.: 192,564

[22] Filed: Sep. 30, 1980

Related U.S. Application Data

[63] Continuation of Ser. No. 926,999, Jul. 21, 1978, abandoned.

[30] Foreign Application Priority Data

Jul. 28, 1977 [FR] France ............... 7723222
Feb. 15, 1978 [FR] France ............... 7804207

[51] Int. Cl.³ .................. A01N 9/22; C07D 239/30; C07D 239/38; C07D 239/48
[52] U.S. Cl. .................... 71/92; 544/122; 544/292
[58] Field of Search ............ 544/298; 71/92

[56] References Cited

U.S. PATENT DOCUMENTS

| | | | |
|---|---|---|---|
| 3,843,656 | 10/1974 | Obellianne et al. | 544/298 |
| 3,892,554 | 7/1975 | Schneider | 71/92 |
| 3,926,997 | 12/1975 | Fisher et al. | 71/92 |
| 3,968,214 | 7/1976 | Claverie et al. | 544/298 |
| 4,051,244 | 9/1977 | Mattioda et al. | 544/298 |
| 4,082,535 | 4/1978 | Hoegerl et al. | 71/92 |
| 4,116,674 | 9/1978 | Sunley et al. | 71/92 |
| 4,166,852 | 9/1979 | Loiseau et al. | 544/298 |

FOREIGN PATENT DOCUMENTS

| | | |
|---|---|---|
| 841390 | 11/1976 | Belgium . |
| 2119234 | 8/1972 | France . |
| 2173746 | 10/1973 | France . |
| 92789 | 8/1978 | Japan . |

OTHER PUBLICATIONS

Toyama et al., "Chemical Abstracts", vol. 90, 1979, Col. 54968y.
Mattioda et al., "J. Med. Chem.", vol. 18, No. 6, 1975, pp. 553–559.
Nantka-Namirski et al., "Chemical Abstracts", vol. 74, 1971, col. 31766m.
Mossini et al., "Chemical Abstracts", vol. 89, 1978, col. 101721d.

Primary Examiner—Glennon H. Hollrah
Assistant Examiner—James H. Turnipseed
Attorney, Agent, or Firm—Beveridge, DeGrandi & Weilacher

[57] ABSTRACT

Pyrimidine compounds of the formula:

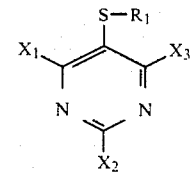

(I)

in which $R_1$ is alkyl, one of $X_1$, $X_2$, $X_3$ is chlorine or bromine and the two others are respectively $-NR_1R_2$ and $-NR_3R_4$ in which $R_2$ and $R_3$ are, independently of one another, hydrogen, alkyl, cycloalkyl, aryl or aryl substituted by alkyl, hydroxy, chlorine, bromine or

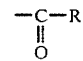

wherein R is hydrogen or alkyl, or form together with the nitrogen atom to which they are linked a nitrogenous heterocyclic radical other than piperazino and substituted piperazino, $R_4$ and $R_5$ are, independently of one another, hydrogen, alkyl, cycloalkyl, aryl or aryl substituted by alkyl, hydroxy, chlorine, bromine or

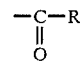

wherein R is as defined above, or form together with the nitrogen atom to which they are linked a nitrogenous heterocyclic radical other than piperazino and substituted piperazino, at least one of the substituents $-NR_1R_2$, $-NR_3R_4$ being $NH_2$ or

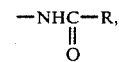

and their salts with mineral or organic acids, are herbicides.

16 Claims, No Drawings

2-(OR4-)AMINO-5-ALKYLTHIO-PYRIMIDINE HERBICIDES

This is a continuation of application Ser. No. 926,999 filed July 21, 1978 and now abandoned.

BACKGROUND OF THE INVENTION

1. Field of the Invention

The present invention relates to new 5-alkylthio-pyrimidines bearing an amino or acylamino group, their methods of preparation and their applications as herbicides.

2. Description of the Prior Art

Herbicidal derivatives of pyrimidine are known (see for example the French Pat. Nos. 2,031,422; 2,317,291; 2,119,234 and 2,137,933). However, these derivatives never simultaneously carry an alkylthio group in position 5 and an amino or acylamino group.

SUMMARY OF THE INVENTION

The new 5-alkylthio-pyrimidines according to the invention may be represented by the general formula:

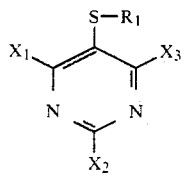

(I)

in which $R_1$ is alkyl containing 1 to 5 carbon atoms, one of the substituents $X_1$, $X_2$, $X_3$ is chlorine or bromine, preferably chlorine, and the two others are respectively:

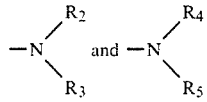

in which $R_2$ and $R_3$ represent, independently of one another, hydrogen, alkyl containing 1 to 5 carbon atoms, cycloalkyl containing 3 to 6 carbon atoms, aryl containing 6 to 12 carbon atoms or said aryl substituted by alkyl containing 1 to 5 carbon atoms, hydroxy, chlorine or bromine, or

wherein R is hydrogen or alkyl containing 1 to 5 carbon atoms, or form together with the nitrogen atom to which they are linked a nitrogenous heterocyclic radical other than piperazino and substituted piperazino, $R_4$ and $R_5$ represent, independently of one another, hydrogen, alkyl containing 1 to 5 carbon atoms, cycloalkyl containing 3 to 6 carbon atoms, aryl containing 6 to 12 carbon atoms or said aryl substituted by alkyl containing 1 to 5 carbon atoms, hydroxy, chlorine or bromine, or

wherein R is as defined above, or form together with the nitrogen atom to which they are linked a nitrogenous heterocyclic radical other than piperazino and substituted piperazino, at least one of the substituents:

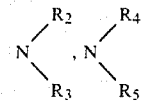

being $NH_2$ or

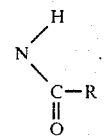

In the definitions given above for $R_2$, $R_3$, $R_4$, $R_5$, cycloalkyl is preferably cyclohexyl and aryl is preferably phenyl. Examples of nitrogenous heterocyclic radicals include piperidino, morpholine and 2,6-dimethyl-morpholino.

DESCRIPTION OF THE PREFERRED EMBODIMENTS

While the present invention relates broadly to the compounds of formula (I), it is more particularly directed to those compounds wherein $X_1$ is chlorine, one of $X_2$ and $X_3$ is $NH_2$ or

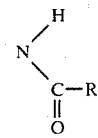

and the other is $NH_2$,

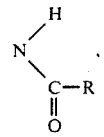

monoalkylamino in which the alkyl contains 1 to 5 carbon atoms, dialkylamino in which the alkyl contains 1 to 5 carbon atoms, piperidino or morpholino.

The compounds of formula (I) in which $R_2$, $R_3$, $R_4$, $R_5$ are other than

and in which then at least one of the substituents

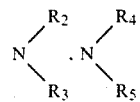

is an $NH_2$ group, can be prepared by condensation of a 2,4,6-trihalo-5-alkylthio-pyrimidine of formula (II) with a compound of formula (III) and condensation of the 4,6-(or 2,6-)dihalo-5-alkylthio-pyrimidine of formula (IV) or (IV) bis thus obtained with a compound of formula (V), according to the reaction diagram:

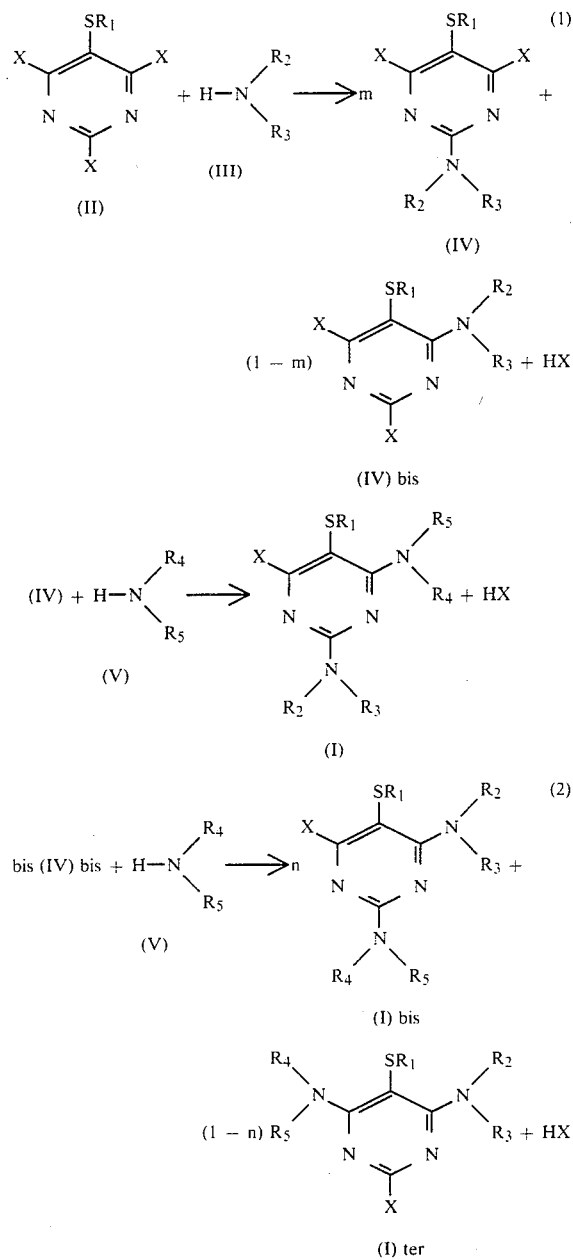

In the formulae (II) to (V), X is chlorine or bromine and $R_1$, $R_2$, $R_3$, $R_4$ and $R_5$ have the same definitions as in formula (I) except, for $R_2$ to $R_5$, the significance

and m and n are numbers greater than 0 and less than 1. One at least of the compounds (III) and (V) is then necessarily ammonia.

The 2,4,6-trihalo-5-alkylthio-pyrimidines of formula (II) are known products. They may be prepared, for example, by the process described in French Pat. No. 1,549,494 applied for on Oct. 31, 1967.

The condensation reactions (1), (2) and (2) bis may be effected either in an aqueous medium, or in an organic solvent medium, or also in a mixed water + organic solvent medium. Organic solvents which can be used include, in particular, without the invention being restricted thereto, toluene, methanol, aliphatic ketones such as acetone, methylethylketone or diethylketone, dimethylformamide or an excess of compound (III) or (V), when this is an amine.

The condensation reactions (1), (2) and (2) bis are effected in the presence of a basic agent capable of fixing the halohydric acid HX formed in the reaction. Examples of basic agents which may be used include alkali metal hydroxides, ammonia, or an excess of the compounds of formulae (III) or (V).

The reactions (1), (2) and (2) bis are effected at a temperature which is a function especially of the solvent used. Generally the reaction (1) is effected between 0° and 150° C. It may then be carried out at a temperature lower than ordinary temperature, for example, between 0° and 10° C., or at a temperature greater than ordinary temperature, for example, between 100° and 150° C. Reactions (2) and (2) bis cannot be carried out at temperatures as low as those utilizable for reaction (1). They are generally effected between 100° and 150° C. According to the temperature and the solvent used, reactions (1), (2) and (2) bis are effected at atmospheric pressure or under a pressure greater than the atmospheric pressure, e.g., from 1 to 30 atmospheres.

The dihalo-5-alkylthio-pyrimidine isomers (IV) and (IV) bis obtained in reaction (1) may be separated, for example, by fractional crystallization. The isomers thus separated then give, by reactions (2) and (2) bis, the pure compound (I) and a mixture of the two isomeric compounds (I) bis and (I) ter.

The mixture of compounds (IV) and (IV) bis obtained in reaction (1) can also be subjected to the second stage of the process, i.e., reaction with the compound (V). Then a mixture of the three isomeric compounds (I), (I) bis and (I) ter is obtained which can be employed as such in herbicide applications. The isomeric compounds (I), (I) bis and (I) ter may also be separated by liquid chromatography.

In the case wherein the compounds (III) and (V) are identical and are then both ammonia, the isomeric compounds (I) and (I) bis are identical and the whole of the preceding reaction diagram leads to the two isomeric compounds of formulae (VI) and (VII) below. In this same case, and on the condition the operation is effected at a sufficiently high temperature (100° to 150° C. in practice), there can be obtained from the 2,4,6-trihalo-5-alkylthio-pyrimidine of formula (II), in a single stage, a mixture of the isomeric compounds (VI) and (VII), according to the reaction:

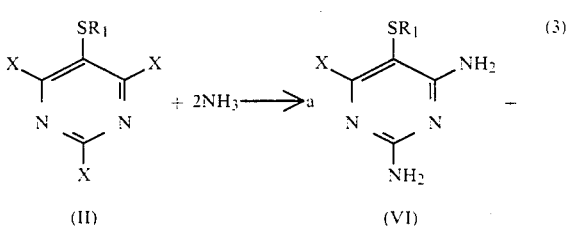

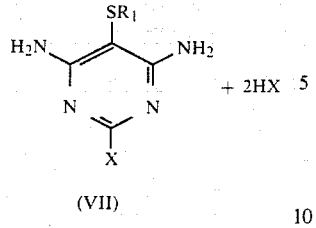 + 2HX (5)

In this mixture compound (VI) is predominant, that is to say, a is lower than 1 and higher than 0.5 in equation (3) above.

The compounds of formula (I) in which $X_1$ is chlorine or bromine, $X_3$ is $NH_2$ and $X_2$ is

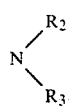

wherein $R_2$ and $R_3$ are identical alkyl groups R' may also be prepared by reaction of a 2,4,6-trihalo-5-alkylthio-pyrimidine of formula (II) with a tertiary amine of formula (VIII) and condensation of the 4,6-dihalo-5-alkylthio-pyrimidine of formula (IX) thus obtained with ammonia, according to the following reaction diagram

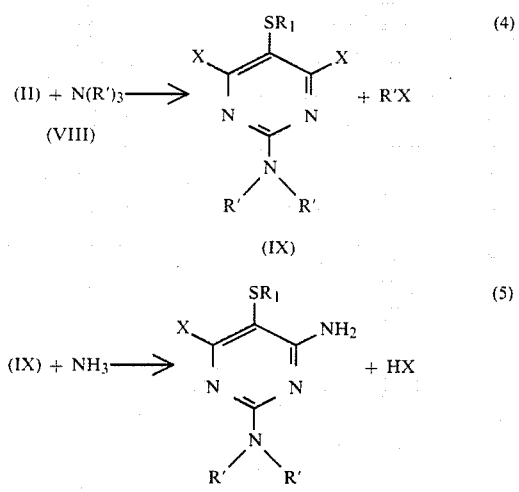

Reaction (4), which shows the originality of providing selectively the isomer 4,6-dihalo-5-alkylthio-pyrimidine, may be effected in an organic solvent medium, at a temperature between 100° to 150° C. The organic solvents to be used may be the same solvents as for reactions (1), (2) and (2) bis.

Reaction (5) is carried out under the same conditions as reaction (2).

The compounds formed in reactions (1), (2), (2) bis, (3), (4) and (5) may be isolated from the reaction medium by conventional methods such as, for example, filtration when the compounds are precipitated, or distillation under reduced pressure of the solvent followed by washing the residue with water, and purified by recrystallization in a suitable solvent.

The compounds of formula (I) in which one at least of the substituents $R_2$, $R_3$, $R_4$, $R_5$ is

may be prepared by acylation of the compounds of formula (I) in which $R_2$, $R_3$, $R_4$, $R_5$ are other than

This acylation is effected by means of the usual acylating agents such as acid chlorides, acid anhydrides, ketene or homologous compounds. The operation is effected in an organic solvent medium, at a temperature between 20° and 120° C., preferably between 50° and 100° C. Organic solvents which may be used include in particular carboxylic acids, in the case where the acylation is carried out with an acid anhydride, and pyridine, in the case where the acylation is effected with an acid chloride.

The compounds of formula (I) may be converted into their salts with mineral or organic acids by reaction with the corresponding acid in a suitable solvent.

The compounds of formula (I) and their salts with the mineral or organic acids have the property of destroying a large number of undesirable plants belonging to the classes of monocotyledons or dicotyledons and accomplishing this with very small doses between 150 g/ha and 2500 g/ha. In particular, they totally destroy the following plants: rye grass, panic grass, digitaria, setaria, foxtail grass, wild oats, yellow bedstraw, amarant polygonum or knot-grass, casswed or shepherd's purse, speedwell, mustard, stinkweed, chickweed, stellaria or starwort, thistle, fumitory, goosefoot, sorrel, plantain, atriplex, dandelion, red poppy, chrysanthemum, groundsel, sow-thistle or milkweed and spurge. In addition, at doses at which they are active towards the undesirable plants, the compounds of formula (I) and their salts do not have in general an unfavorable action on winter and spring cereals such as wheat and barley, or on rice and maize.

The compounds of formula (I) and their salts are active towards adventitious plants both in pre-emergence treatments and in post-emergence treatments. However, their activity is more marked in the post-emergence treatments.

For their use the herbicidal compounds according to the invention can be incorporated, jointly with other herbicides or separately, in formulations which contain, beside a herbicidally effective amount of the active material, inert additives normally used in agriculture for facilitating conservation, putting in aqueous suspension, adherence to foliage and resistance to atmospheric agents and biological degradations (hence a greater persistence of action), such as solid diluents or carriers (talc, silica, kieselguhr, clay, etc.) or liquid diluents or carriers, (mineral oils, water, organic solvents such as, for example, ketones, alcohols, hydrocarbons or their chlorinated derivatives), adjuvants, surface-active substances, antioxidants and stabilizers. Such formulations can appear in the form of wettable powders, solutions emulsifiable in water, suspensions, granules or any other form in use in the field of herbicides.

In the formulations containing only the herbicidal compounds according to the invention and inert additives, the content of compounds of formula (I) or their salts (active material) may vary from 1% to 95% by weight. In the formulations containing the herbicidal compounds according to the invention, other herbicides and inert additives, the content of compounds according to the invention may vary from 1% to 80% by weight, that of other herbicides from 80% to 1% by weight, the complement to 100% consisting of the inert additives.

Examples of other herbicides which may be associated with the compounds according to the invention in the formulations include 3-(3,4-dichloro-phenyl)-1,1-dimethyl-urea (diuron), 3-phenyl-1,1-dimethyl-urea (fenuron), 3-(3-chloro-4-methyl-phenyl)-1,1-dimethyl-urea (chlortoluron), 3-(4-chloro-phenyl)-1,1-dimethyl-urea (monuron), monolinuron, 3-(3,4-dichloro-phenyl)-1-methoxy-1-methyl-urea (linuron), isoproturon, mithabenzthiazuron, 3-(3,4-dichloro-phenyl)-1-n-butyl-1-methyl-urea (neburon), 2-chloro-4-ethylamino-6-isopropylamino-1,3,5-triazine (atrazine), 2-chloro bis 4,6-(ethylamino)-1,3,5-triazine (simazine), 3-amino-1,2,4-triazole, terbutryne, cyanazine, 2,6-diethyl-N-chloroacetyl-N-methoxymethyl-aniline (alachlor), N-chloroacetyl-N-isopropyl-aniline (propachlor), napropamide, diquat, paraquat, 2,4-dichloro-phenoxyacetic acid (2,4-D), 2-(2-methyl-4-chloro-phenoxy)-propionic acid (MCPP), 2-methoxy-3,6-dichloro-benzoic acid (dicamba), 4-amino-3,5,6-trichloro-picolinic acid (picloram), 2,4-dinitro-6-sec-butyl-phenol (dinoseb), 4,6-dinitro-ortho-cresol (DNOC), N-(3-chloro-phenyl) carbamate of 4-chloro-2-butynyle (barban), propham, terbacile, 5-bromo-3-sec-butyl-6-methyl-uracil (bromacile) pyrazone, phenmedipham and metamitron.

The following examples illustrate the invention without it being restricted thereto. In the examples and throughout the specification and claims all weights and percentages are by weight unless otherwise defined.

EXAMPLE 1

4-amino-6-chloro-2-ethylamino-5-methylthio-pyrimidine.

The preparation of this compound is effected in 2 stages.

FIRST STAGE 45.9 Grams of 2,4,6-trichloro-5-methylthio-pyrimidine, 150 g of methylethylketone and 130 g of water are introduced into a 250 ml reactor provided with a stirrer. To this mixture maintained at 5° C. are added in a period of 30 minutes 9.44 g of ethylamine in 32.5% aqueous solution. The temperature of 5° C. is maintained for one and one half hours. Then 8.08 g of caustic soda in 30% aqueous solution are added. The mixture is maintained at 20° C. for 4 hours and over night in a refrigerator at about 0° C. A precipitate appears which is isolated by filtration, washed with 16 ml of methylethylketone and recrystallized twice from 180 ml of ethanol. 10.5 G of 2-ethylamino-4,6-dichloro-5-methylthio-pyrimidine are thus obtained, which melts at 147° C. and which is identified by its infra-red spectrum (IR) and it nuclear magnetic resonance spectrum (NMR).

The filtrate is evaporated. 36.5 G of a mixture of 2-ethylamino-4,6-dichloro-5-methylthio-pyrimidine and 4-ethylamino-2,6-dichloro-5-methylthio-pyrimidine are thus obtained, which mixture melts at 76° C. and is identified by its IR and NMR spectra.

SECOND STAGE 7.5 Grams of 2-ethylamino-4,6-dichloro-5-methylthio-pyrimidine obtained as indicated above, 110 ml of methanol and 11 g of ammonia are introduced into a 500 ml autoclave. The mixture is heated at 110° C. for 2 hours, then cooled. The solution obtained is concentrated under reduced pressure and the residue is washed with water. 8.2 g of 4-amino-6-chloro-2-ethylamino-5-methylthio-pyrimidine are thus obtained, which is identified by its IR and NMR spectra and which melts at 124° C.

EXAMPLE 2

Mixture of the three isomers 4-amino-6-chloro-2-ethylamino-5-methylthio-pyrimidine, 2-amino-6-chloro-4-ethylamino-5-methylthio-pyrimidine and 2-chloro-6-amino-4-ethylamino-5-methylthio-pyrimidine.

2.5 Grams of 2-ethylamino-4,6-dichloro-5-methylthio-pyrimidine, 9 g of the mixture of 2-ethylamino-4,6-dichloro-5-methylthio-pyrimidine and 4-ethylamino-2,6-dichloro-5-methylthio-pyrimidine obtained in the first stage of Example 1, 165 g of methanol and 16 g of ammonia are introduced into a 500 ml autoclave. The mixture is heated for 2 hours at 120° C., then cooled. The solution obtained is concentrated under reduced pressure and the residue is washed with water. 8.2 Grams of a mixture melting at 76° C. are thus obtained. The analysis of the mixture by gas chromatography and mass spectrometry shows that it contains 56.6% of 2-amino-6-chloro-4-ethylamino-5-methylthio-pyrimidine, 37.8% of 4-amino-2-ethylamino-6-chloro-5-methylthio-pyrimidine and 5.6% of 6-amino-4-ethylamino-2-chloro-5-methylthio-pyrimidine.

EXAMPLE 3

Mixture of the three isomers 2-amino-6-chloro-4-isopropylamino-5-methylthio-pyrimidine, 4-amino-6-chloro-2-isopropylamino-5-methylthio-pyrimidine and 6-amino-4-isopropylamino-2-chloro-5-methylthio-pyrimidine.

The synthesis is carried out in 2 stages.

FIRST STAGE

The first stage of Example 1 is repeated with the exception that the ethylamine is replaced by 11.8 g of -isopropylamine. By evaporation under reduced pressure of the final solution, washing of the residue with water and drying under reduced pressure, 51.4 g of a paste constituted by a mixture of 4,6-dichloro-2-isopropylamino-5-methylthio-pyrimidine and 2,6-dichloro-4-isopropylamino-5-methylthio-pyrimidine are obtained.

SECOND STAGE 12.5 Grams of the mixture obtained in the first stage. 250 g of methanol and 25 g of ammonia are introduced into a 500 ml autoclave. After heating for 2 hours at 130° C., the solution obtained is concentrated under vacuum and the residue is washed with water. 12.1 g of a pasty product are thus obtained, which, as shown by gas chromatography and mass spectrometry, is a mixture containing 55.1% of 2-amino-6chloro-4-isopropylamino-5-methylthio-pyrimidine, 39.4% of 4-amino-6-chloro-2-isopropylamino-5-methylthio-pyrimidine and 5.5% of 4-isopropylamino-6-amino-2-chloro-5-methylthio-pyrimidine.

EXAMPLE 4

Mixture of the three isomers 2-amino-6-chloro-4-methylamino-5-methylthio-pyrimidine, 4-amino-6-chloro-2-methylamino-5-methylthio-pyrimidine and 6-amino-2-chloro-4-methylamino-5-methylthio-pyrimidine.

The synthesis is carried out in two stages.

FIRST STAGE

The first stage of Example 1 is repeated with exception that the ethylamine is replaced by 6.2 g of methylamine in 30.7% solution in water. After the reaction, 13 g of a precipitate consisting of 4,6-dichloro-2-methylamino-5-methylthio-pyrimidine melting at 142° C. are obtained by filtration.

By concentration under reduced pressure of the filtrate and washing the residue with water, 33.4 g of a product melting at 91° C. are obtained which, as shown by IR and NMR spectra, is a mixture of 4,6-dichloro-2-methylamino-5-methylthio-pyrimidine and 2,6-dichloro-4-methylamino-5-methylthio-pyrimidine.

SECOND STAGE

8 Grams of 4,6-dichloro-2-methylamino-5-mthylthio-pyrimidine, 20.6 g of the mixture of the two isomers obtained in the first stage, 50 g of ammonia and 350 g of methanol are introduced into a 500 ml autoclave. After heating at 130° C. for two hours, the solution obtained is concentrated under vacuum and the residue is washed with water. 20.6 g of a mixture melting at 118° C. are thus obtained. As shown by gas chromatography and mass spectrometry, this mixture contains 50.3% of 2-amino-4-methylamino-6-chloro-5-methylthio-pyrimidine, 48.3% of 4-amino-2-methylamino-6-chloro-5-methylthio-pyrimidine and 1.4% of 6-amino-4-methylamino-2-chloro-5-methylthio-pyrimidine.

EXAMPLE 5

Mixture of 2-amino-6-chloro-4-ethylamino-5-methylthio-pyrimidine and 6-amino-2-chloro-4-ethylamino-5-methylthio-pyrimidine.

The synthesis is carried out in two stages.

FIRST STAGE

The first stage of Example 1 is repeated using 18 g of ethylamine in 32.5% solution in water, 91.8 g of 2,4,6-trichloro-5-methylthio-pyrimidine, 300 g of methylethylketone, 260 g of water and 16.2 g of caustic soda.

At the end of the reaction, 25.5 g of 4,6-dichloro-2-ethylamino-5-methylthio-pyrimidine are collected by filtration. The filtrate is concentrated under reduced pressure, the residue obtained is dissolved in 280 ml of concentrated hydrochloric acid and 112 ml of water are added to the solution obtained. On filtration, 11.5 g are obtained of a mixture of 4,6-dichloro-2-ethylamino-5-methylthio-pyrimidine and 2,6-dichloro-4-ethylamino-5-methylthio-pyrimidine. A further 2 liters of water are added to the filtrate. On further filtration, 36 g of 2,6-dichloro-4-ethylamino-5-methylthio-pyrimidine of melting point 80° C. are obtained.

SECOND STAGE

18 Grams of 2,6-dichloro-4-ethylamino-5-methylthio-pyrimidine, 220 ml of methanol and 40 g of ammonia are introduced into a 500 ml autoclave. After heating for 2 hours at 130° C., the solution is evaporated under reduced pressure. By crystallization of the residue from an ethanol-water mixture, 10.8 g of a mixture melting at 100° C. are obtained. As shown by gas chromatography and mass spectrometry, this mixture contains 94.4% of 2-amino-4-ethylamino-6chloro-5-methylthio-pyrimidine and 5.6% of 6-amino-4-ethylamino-2-chloro-5-methylthio-pyrimidine.

EXAMPLE 6

6-chloro-2,4-diamino-5-ethylthio-pyrimidine.

A mixture of 24.6 g of barbituric acid, 20 g of diethylsulfoxide, 75 ml of glacial acetic acid and 28 ml of acetic anhydride is heated at 95° C. for five and one-half hours. After cooling, 175 ml of water are added in the cold. The precipitate obtained is filtered off, washed with acetone and dried under reduced pressure; 21.7 g of 5-diethyl-sulphonium barbiturylide are thus obtained.

84.4 Grams of phosphorus oxychloride and 5 ml of dimethylaniline are added to 21.7 g of 5-diethylsulphonium-barbiturylide and the mixture obtained is heated at the boil for 20 hours. After cooling to 60° C., the reaction mixture is poured onto ice and stirred for 1 hour. The precipitate obtained is filtered off, dried and recrystallized from hexane. 10 Grams of 2,4,6-trichloro-5-ethylthio-pyrimidine melting at 62°-64° C. are thus obtained.

10 Grams of 2,4,6-trichloro-5-ethylthio-pyrimidine, 17 g of ammonia and 100 g of methanol are introduced into a 500 ml autoclave. After reaction at 100° C. for 2 hours, the precipitate obtained is filtered off, washed with water and dried under reduced pressure. 5.6 Grams of a product melting at 182° C. and consisting essentially of 6-chloro-2,4-diamino-5-ethylthio-pyrimidine are thus obtained. This product is characterized by its IR, NMR and mass spectra.

EXAMPLE 7

6-chloro-2,4-diamino-5-butylthio-pyrimidine.

120 Grams of methanol, 20 g of ammonia and 17 g of 2,4,6-trichloro-5-butylthio-pyrimidine are heated at 100° C. for two hours in a 500 ml autoclave. After cooling, the solution obtained is concentrated under reduced pressure. The residue obtained is washed with water, and recrystallized from propanol. 7 Grams of a product melting at 129° C. and consisting essentially of 5-chloro-2,4-diamino-5-butylthio-pyrimidine are thus obtained. This product is characterized by its IR, NMR and mass spectra.

The 2,4,6-trichloro-5-butylthio-pyrimidine used as starting material is prepared by the process described in Example 6 for the preparation of 2,4,6-trichloro-5-ethylthio-pyrimidine, by replacing initially the diethyl sulfoxide by dibutyl sulfoxide.

EXAMPLE 8

Mixture of 6-chloro-2,4-diamino-5-methylthio-pyrimidine (isomer A) and 2-chloro-4,6-diamino-5-methylthio-pyrimidine (isomer B).

2.5 Liters of methanol, 250 g of ammonia and 250 g of 2,4,6-trichloro-5-methylthio-pyrimidine are introduced into a 5 liter autoclave and heated at 100° C. for 2 hours. The solution obtained is concentrated under reduced pressure and ether is added to the residue obtained. The part insoluble in the ether is separated, washed with water and dried. 153.7 Grams of a mixture of isomers A and B, in which isomer A is predominant, are thus obtained. This mixture melts at 145° C. and is characterized by its IR and NMR spectra.

EXAMPLE 9

4-amino-6-chloro-2-diethylamino-5-methylthio-pyrimidine.

100 Grams of toluene, 23 g of 2,4,6-trichloro-5-methylthio-pyrimidine and 10.1 g of triethylamine are heated at the boiling point for 3 hours in a round-bottomed flask of 500 ml provided with a cooling device. The solution obtained is concentrated under reduced pressure and the residue is introduced into a 500 ml autoclave with 350 ml of methanol and 50 g of ammonia. The solution obtained after 2 hours reaction at 130° C. is concentrated again under reduced pressure. A residue is obtained which is washed with water and recrystallized from a water-alcohol mixture. 17.5 Grams of 4-amino-6-chloro-2-diethylamino-5-methylthio-pyrimidine melting at 68° C. are thus obtained, which product is characterized by its IR and NMR spectra,

EXAMPLE 10

2-methylamino-4-amino-6-chloro-5-methylthio-pyrimidine.

This compound is obtained by the method of operation of Example 1 with the exception that in the first stage the ethylamine is replaced by methylamine. It melts at 205° C. and is characterized by its IR and NMR spectra.

EXAMPLE 11

Mixture of 4-methylamino-2-amino-6-chloro-5-methylthio-pyrimidine and 2-chloro-4-methylamino-6-amino-5-methylthio-pyrimidine.

This mixture is obtained by the method of operation of Example 5 with the exception that in the first stage the ethylamine is replaced by methylamine. It melts at 139° C. and is characterized by its IR and NMR spectra.

EXAMPLE 12

2-piperidine-4-amino-6-chloro-5-methylthio-pyrimidine.

This compound is obtained by the method of operation of Example 1 with the exception that in the first stage the ethylamine is replaced by piperidine. It melts at 128° C. and is characterized by its IR and NMR spectra.

EXAMPLE 13

2-morpholino-4-amino-6-chloro-5-methylthio-pyrimidine.

The compound is obtained by the method of operation of Example 1 with the exception that in the first stage the ethylamine is replaced by morpholine. It melts at 115° C. and is characterized by its IR and NMR spectra.

EXAMPLE 14

4-acetylamino-2-diethylamino-6-chloro-5-methylthio-pyrimidine

250 Ml of acetic acid and 25 g of 4-amino-6-chloro-2-diethylamino-5-methylthio-pyrimidine prepared as described in Example 9 are placed in a 500 ml round-bottomed flask provided with a cooling device and a stirrer. The mixture is heated to 50° C. and then 50 ml of acetic anhydride are progressively introduced, after which it is heated under reflux for 30 minutes. It is then evaporated under vacuum and the residue is taken up in water three times in order to hydrolyze the excess of acetic anhydride.

The crude product obtained is then recrystallized from ethanol. A product which melts at 72°–73° C. is thus obtained. The analysis by NMR and IR confirms that this product is 4-acetylamino-6-chloro-2-diethylamino-5-methylthio-pyrimidine.

EXAMPLE 15

Mixture of 2,4-diamino-6-chloro-5-methylthio-pyrimidine (isomer A) and 4,6-diamino-2-chloro-5-methylthio-pyrimidine (isomer B).

1300 Grams of 2,4,6-trichloro-5-methylthio-pyrimidine. 1700 ml of isopropanol and 495 g of ammonia are introduced into a 5 liter autoclave and heated at 100° C. for 5 hours. After cooling to ambient temperature, the precipitate formed is filtered off, washed with 700 ml of isopropanol and then with water, and dried. 1010 Grams of a mixture of isomers A and B are thus obtained, which corresponds to a yield of 93.6% with respect to the 2,4,6-trichloro-5-methylthio-pyrimidine used.

This mixture melts at 160° C. Its analysis by thin-layer chromatography with silica as support and a 90/10 chloroform-methanol mixture as eluent, by gas chromatography coupled with mass spectrometry, by IR spectrometry and by nuclear magnetic resonance of carbon 13 shows that it contains approximately 89% of isomer A and 11% of isomer B.

EXAMPLE 16

2,4-diamino-6-chloro-5-methylthio-pyrimidine (isomer A).

10 Grams of the mixture obtained in Example 15 are dissolved in 85 ml of concentrated hydrochloric acid and 55 ml of water are gradually added to the solution obtained. The precipitate formed is filtered off, washed with water and dried and 2.9 g of a product consisting essentially of isomer A are thus obtained.

EXAMPLE 17

Mixture of 2,4-diamino-6-chloro-5-methylthio-pyrimidine (isomer A) and 4,6-diamino-2-chloro-5-methylthio-pyrimidine (isomer B), which is richer in isomer B.

FIRST STAGE

46 Grams of finely ground 2,4,6-trichloro-5-methylthio-pyrimidine are dispersed under stirring in 500 ml of water containing 1.2 g of the product known under the trademark PLURONIC L 92 (non-ionic surface-active compound consisting of a copolymer of ethylene oxide and propylene oxide). Then 170 g of a 20% aqueous solution of ammonia are introduced within 10 minutes, the temperature of 5° C. being maintained. Then the mixture is maintained at ambient temperature overnight and the precipitate formed is filtered off and washed with water. 42 Grams of product are thus collected. As shown particularly by the analysis by nuclear magnetic resonance of carbon 13, this product is a mixture of the two isomeric compounds 4,6-dichloro-2-amino-5-methylthio-pyrimidine and 2,6-dichloro-4-amino-5-methylthio-pyrimidine.

SECOND STAGE

40 Grams of the mixture obtained in the first stage are dissolved in 700 ml of concentrated hydrochloric acid and 200 ml of water are added to the solution obtained. A precipitate is formed, which is separated by filtration. and 120 ml of water are added to the filtrate. A new precipitate b is formed, which is separated by filtration. Finally, 260 ml of water and then 200 ml of a N/10 solution of sodium hydroxide are added to the filtrate. A precipitate c is formed, which is separated by filtration.

The precipitate a (weight 6 g) is essentially constituted by 4,6-dichloro-2-amino-5-methylthio-pyrimidine. The precipitate c (weight 17.2 g) is formed by 2,6-dichloro-4-amino-5-methylthio-pyrimidine.

THIRD STAGE 16.5 Grams of precipitate c obtained in the second stage, 150 ml of isopropanol and 17 g of ammonia are introduced in an autoclave. The mixture is heated at 100° C. for three hours and fifteen minutes. After cooling, the precipitate formed is filtered off and 11.3 g of a product which is a mixture of isomers A and B are thus obtained. The percentage of isomer B in the mixture is 20%.

EXAMPLE 18

2,4-diamino-6-chloro-5-methylthio-pyrimidine (isomer A) and 4,6-diamino-2-chloro-5-methylthio-pyrimidine (isomer B).

Isomers A and B are separated by liquid chromatography, starting from the mixture obtained in the third stage of Example 17.

The mixture is dissolved in chloroform to which 2.5% of ethanol has been added. The solution is introduced at the top of a column having a length of 25 cm and an inner diameter of 22 mm, which is filled with a silica gel having a particle size of 5μ available as LICHROSORB Si 60. The elution is effected with chloroform to which 2.5% of ethanol has been added. The fractions collected at the bottom of the column by means of a fractions collector are evaporated and 2.1 g of 2,4-diamino-6-chloro-5-methylthio-pyrimidine, which has a melting point of 171° C. and 0.9 g of 4,6-diamino-2-chloro-5-methylthio-pyrimidine, which has a melting point of 270° C. are thus obtained.

EXAMPLE 19

In this example, the products according to the invention are formulated as aqueous suspensions containing 5% of a surface-active substance available as "TWEEN 20".

The amounts of suspensions applied are equivalent to 1000 l/ha, and the dilutions used are calculated to provide the following quantities of active material:

$D_1 = 2.5$ Kg/ha $D_2 = 10$ Kg/ha

The suspensions are applied by spraying either of them on plants 10 days old, which allows the post-emergence action of the products to be studied, or on seeds deposited at the surface of the soil, which enables the pre-emergence action to be studied. These seeds are covered with 2 cm of earth just after the application.

The plants and seeds are placed in plastic containers having the dimensions $18 \times 12 \times 5$ cm filled with a standard soil composed of 3 parts of sand, 1 part of compost and 1 part of clay. After treatment, the containers are placed on a shelf with automatic irrigation in a greenhouse maintained at 22° C. and at a relative atmospheric humidity of 70%.

The plants subjected to the tests are wheat TRITICUM SP, bean PHASEOLUS SP, beetroot BETA SP, mustard SINAPIS SP, dandelion TARAXACUM SP and maize ZEA SP.

The results were recorded 14 days after treatment for the post-emergence tests and 21 days after treatment for the pre-emergence tests.

The results are tabulated in Table No. I. In this table the herbicidal efficiency of the compounds of the invention towards the tested plants is expressed by a figure which represents the percentage of destruction of the plants in the treated batches. This percentage is evaluated by taking as reference the plants of untreated control batches. The FIG. 0 indicates that the state of the plants is the same in the treated batches and in the control batches, and the FIG. 100 indicates that the plants are entirely destroyed in the treated batches, which corresponds to the maximum efficiency.

TABLE 1

Efficiency expressed by the percentage of destruction

| Product of Example | POST-EMERGENCE | | | | | | | | | | | |
|---|---|---|---|---|---|---|---|---|---|---|---|---|
| | $D_1 = 2.5$ kg/ha | | | | | | $D_2 = 10$ kg/ha | | | | | |
| | wheat | bean | beetroot | mustard | dandelion | maize | wheat | bean | beetroot | mustard | dandelion | maize |
| 1 | 70 | 100 | — | 100 | 100 | 70 | 75 | 100 | — | 100 | 100 | 100 |
| 2 | 15 | 75 | — | 100 | 100 | 50 | 100 | 100 | — | 100 | 100 | 70 |
| 3 | 20 | 70 | — | 100 | 100 | 70 | 70 | 5C | — | 100 | 100 | 100 |
| 4 | 20 | 50 | — | 100 | 100 | 15 | 50 | 50 | — | 100 | 100 | 15 |
| 5 | 0 | 0 | 100 | 100 | 100 | 0 | 65 | 20 | 100 | 100 | 100 | 0 |
| 6 | 20 | 50 | 100 | 100 | 100 | 15 | 50 | 70 | 100 | 100 | 100 | 70 |
| 7 | 15 | 0 | 100 | 100 | 100 | 0 | 60 | 0 | 100 | 100 | 100 | 0 |
| 8 | 15 | 100 | 100 | 100 | 100 | 0 | 100 | 100 | 100 | 100 | 100 | 15 |
| 9 | 100 | 100 | 100 | 100 | 100 | 50 | 100 | 100 | 100 | 100 | 100 | 100 |
| 10 | 70 | 75 | 100 | 100 | — | 50 | 75 | 100 | 100 | 100 | — | 60 |
| 11 | 0 | 0 | 0 | 0 | — | 0 | 15 | 15 | 50 | 50 | — | 0 |
| 12 | 10 | 15 | 70 | 100 | 15 | 0 | 50 | 100 | 75 | 100 | 50 | 50 |
| 13 | 0 | 50 | 100 | 10 | 100 | 0 | 50 | 50 | 100 | 100 | 100 | 0 |
| 14 | 80 | 100 | 100 | 100 | 0 | 100 | 90 | 100 | 100 | 100 | 50 | |

| Product of Example | PRE-EMERGENCE | | | | | | | | | | | |
|---|---|---|---|---|---|---|---|---|---|---|---|---|
| | $D_1 = 2.5$ kg/ha | | | | | | $D_2 = 10$ kg/ha | | | | | |
| | wheat | bean | beetroot | mustard | dandelion | maize | wheat | bean | beetroot | mustard | dandelion | maize |
| 1 | 0 | 0 | 0 | 0 | 0 | 0 | 15 | 50 | 100 | 100 | 100 | 0 |
| 2 | 15 | 0 | 100 | 100 | 100 | 0 | 50 | 50 | 100 | 100 | 100 | 10 |
| 3 | 0 | 0 | 100 | 100 | 100 | 0 | 50 | 50 | 100 | 100 | 100 | 0 |
| 4 | 0 | 0 | 100 | 10 | 100 | 0 | 0 | 0 | 100 | 100 | 100 | 0 |

TABLE 1-continued

| | Efficiency expressed by the percentage of destruction | | | | | | | | | | | |
|---|---|---|---|---|---|---|---|---|---|---|---|---|
| 5 | 0 | 0 | 0 | 0 | 0 | 0 | 0 | 0 | 0 | 0 | 0 | 0 |
| 6 | — | — | — | — | — | — | — | — | — | — | — | — |
| 7 | — | — | — | — | — | — | — | — | — | — | — | — |
| 8 | 15 | 0 | 100 | 20 | 100 | 0 | 45 | 80 | 100 | 100 | 100 | 0 |
| 9 | 50 | 100 | 100 | 100 | 100 | 0 | 75 | 75 | 100 | 100 | 100 | 0 |
| 10 | 50 | 70 | 10 | 75 | — | 0 | 100 | 100 | 100 | 100 | — | 0 |
| 11 | 0 | 0 | 0 | 0 | — | 0 | 0 | 0 | 0 | 0 | — | 0 |
| 12 | 0 | 0 | 0 | 0 | 0 | 0 | 0 | 0 | 0 | 0 | 0 | 0 |
| 13 | 0 | 0 | 0 | 0 | 0 | 0 | 0 | 0 | 0 | 0 | 0 | 0 |
| 14 | 0 | 0 | 100 | 100 | 100 | 0 | 0 | 0 | 100 | 100 | 100 | 0 |

EXAMPLE 20

The tests are carried out as in Example 19 with only the doses of active material applied being changed. These doses are as follows:

$D_1 = 0.312$ Kg/ha $D_2 = 0.625$ Kg/ha $D_3 = 1.25$ Kg/ha $D_4 = 2.5$ Kg/ha $D_5 = 5$ Kg/ha

The results are tabulated in Tables II and III. The figures given in these tables represent the vegetative energies of the plants of the treated batches, expressed in percentage of the vegetative energy of the plants of the untreated controls. The FIG. 100 indicates that the vegetative energy of the plants of the treated batches is identical with that of the control plants, the FIG. 0 that the plants are entirely destroyed in the treated batches.

In the Tables II and III there are also given the results relative to a reference herbicide (chlortoluron).

TABLE II

POST-EMERGENCE TREATMENT
Vegetative energy expressed in percentage of the controls

| Product of Example | $D_1 = 0.312$ kg/ha | | | | | | $D_2 = 0.625$ kg/ha | | | | | |
|---|---|---|---|---|---|---|---|---|---|---|---|---|
| | wheat | bean | beetroot | mustard | dandelion | maize | wheat | bean | beetroot | mustard | dandelion | maize |
| 1 | — | — | — | — | — | — | 70 | 95 | 0 | 0 | 0 | 100 |
| 2 | — | — | — | — | — | — | 100 | 100 | 75 | 82 | 57 | 100 |
| 3 | — | — | — | — | — | — | 52 | 52 | 0 | 0 | 0 | 75 |
| 4 | — | — | — | — | — | — | 92 | 100 | 5 | 5 | 0 | 92 |
| 8 | 84 | 38 | 8 | 46 | 76 | 100 | 24 | 5 | 0 | 0 | 0 | 100 |
| 9 | 90 | 58 | 0 | 5 | 0 | 91 | 73 | 40 | 0 | 0 | 0 | 89 |
| 14 | 50 | 40 | 0 | 40 | 0 | 100 | 40 | 30 | 0 | 20 | 0 | 100 |
| Chlortoluron* | | | | | | | | | | | | |

| Product of Example | $D_3 = 1.25$ kg/ha | | | | | | $D_4 = 2.5$ kg/ha | | | | | |
|---|---|---|---|---|---|---|---|---|---|---|---|---|
| | wheat | bean | beetroot | mustard | dandelion | maize | wheat | bean | beetroot | mustard | dandelion | maize |
| 1 | 70 | 60 | 0 | 0 | 0 | 91 | 60 | 80 | 0 | 0 | 0 | 82 |
| 2 | 100 | 100 | 17 | 27 | 0 | 100 | 100 | 100 | 12 | 4 | 0 | 100 |
| 3 | 33 | 29 | 0 | 0 | 0 | 77 | 8 | 16 | 0 | 0 | 0 | 34 |
| 4 | 95 | 95 | 0 | 0 | 0 | 85 | 85 | 100 | 0 | 0 | 0 | 80 |
| 8 | 5 | 0 | 0 | 0 | 0 | 100 | 0 | 0 | 0 | 0 | 0 | 100 |
| 9 | 58 | 16 | 0 | 0 | 0 | 90 | 33 | 5 | 0 | 0 | 0 | 64 |
| 14 | 30 | 10 | 0 | 10 | 0 | 100 | 10 | 0 | 0 | 0 | 0 | 100 |
| Chlortoluron* | 87.5 | 22.5 | 17.5 | 0 | 0 | 17.5 | 0.5 | 17.5 | 0 | 0 | 0 | 52.5 |

| Product of Example | $D_5 = 5$ kg/ha | | | | | |
|---|---|---|---|---|---|---|
| | wheat | bean | beetroot | mustard | dandelion | maize |
| 1 | 25 | 47 | 0 | 0 | 0 | 80 |
| 2 | 70 | 97 | 0 | 0 | 0 | 100 |
| 3 | 27 | 4 | 0 | 0 | 0 | 34 |
| 4 | 78 | 88 | 0 | 0 | 0 | 65 |
| 8 | 0 | 0 | 0 | 0 | 0 | 0 |
| 9 | — | — | — | — | — | — |
| 14 | — | — | — | — | — | — |
| Chlortoluron* | | | | | | |

*Reference herbicide

TABLE III

PRE-EMERGENCE TREATMENT
Vegetative energy expressed in percentage of the controls Product

TABLE III-continued

PRE-EMERGENCE TREATMENT
Vegetative energy expressed in percentage of the controls

| Product of Example | $D_1 = 0.312$ kg/ha | | | | | | $D_2 = 0.525$ kg/ha | | | | | |
|---|---|---|---|---|---|---|---|---|---|---|---|---|
| | wheat | bean | beetroot | mustard | dandelion | maize | wheat | bean | beetroot | mustard | dandelion | maize |
| 1 | — | — | — | — | — | — | 100 | 100 | 7 | 40 | 0 | 100 |
| 2 | — | — | — | — | — | — | 100 | 100 | 75 | 82 | 57 | 100 |
| 3 | — | — | — | — | — | — | 85 | 100 | 75 | 17 | 35 | 100 |
| 4 | — | — | — | — | — | — | 100 | 100 | 100 | 100 | 100 | 100 |
| 8 | 70 | 50 | 6 | 18 | 2 | 100 | 94 | 32 | 1 | 0 | 0 | 100 |
| 9 | 100 | 100 | 0 | 0 | 0 | 100 | 100 | 90 | 0 | 0 | 0 | 80 |
| Chlortoluron | — | — | — | — | — | — | — | — | — | — | — | — |

| Product of Example | $D_3 = 1.25$ kg/ha | | | | | | $D_4 = 2.5$ kg/ha | | | | | |
|---|---|---|---|---|---|---|---|---|---|---|---|---|
| | wheat | bean | beetroot | mustard | dandelion | maize | wheat | bean | beetroot | mustard | dandelion | maize |
| 1 | 100 | 100 | 5 | 6 | 0 | 100 | 100 | 100 | 0 | 2 | 0 | 100 |
| 2 | 100 | 100 | 17 | 27 | 0 | 100 | 100 | 100 | 12 | 4 | 0 | 100 |
| 3 | 100 | 100 | 80 | 35 | 17 | 100 | 100 | 72 | 25 | 10 | 20 | 85 |
| 4 | 100 | 100 | 75 | 100 | 25 | 100 | 100 | 95 | 100 | 80 | 20 | 100 |
| 8 | 76 | 13 | 0 | 0 | 0 | 100 | 82 | 9 | 0 | 0 | 0 | 100 |
| 9 | 48 | 21 | 0 | 0 | 0 | 78 | 25 | 10 | 0 | 0 | 0 | 73 |
| Chlortoluron | 100 | 85 | 100 | 85 | 125 | 100 | 100 | 80 | 78 | 79 | 5 | 95 |

| Product of Example | $D_5 = 5$ kg/ha | | | | | |
|---|---|---|---|---|---|---|
| | wheat | bean | beetroot | mustard | dandelion | maize |
| 1 | 100 | 100 | 0 | 0 | 0 | 100 |
| 2 | 70 | 97 | 0 | 0 | 0 | 100 |
| 3 | 100 | 100 | 7 | 7 | 0 | 93 |
| 4 | 100 | 100 | 75 | 48 | 5 | 100 |
| 8 | 74 | 23 | 0 | 0 | 0 | 86 |
| 9 | — | — | — | — | — | — |
| Chlortoluron | — | — | — | — | — | — |

EXAMPLE 21

The tests are conducted as in Example 19, with the following doses of active material:

$D_1 = 0.312$ kg/ha $D_2 = 0.625$ kg/ha $D_3 = 1.25$ kg/ha $D_4 = 2.5$ kg/ha

The plants subjected to the tests are wheat TRITICUM SP, barley ORDEUM SP, oats AVENA SP, rice ORYZA SP, cotton GOSSYPIUM SP, setaria SETARIA SP, panic grass PANICUM SP, digitaria PASPALUM SP and soya bean. The compound according to the invention tested is that of Example 8.

The results obtained are tabulated in Table IV. The significance of the figures in Table IV is the same as that of the figures of Table I. The FIG. 0 indicates that the state of the plants is the same in the treated batches and in the control batches, the FIG. 100 that the plants are entirely destroyed in the treated lots.

TABLE IV

Percentage of destruction of the plants

| Product of Example 8 | Pre-emergence Treatment Treated plants | | | | | | | | |
|---|---|---|---|---|---|---|---|---|---|
| Dose in kg/ha | wheat | barley | oats | soya bean | rice | cotton | panic | setaria | digitaria |
| $D_1 = 0.312$ | 0 | 0 | 0 | 0 | 0 | 0 | 0 | 0 | 0 |
| $D_2 = 0.625$ | 0 | 0 | 8 | 0 | 0 | 0 | 0 | 0 | 0 |
| $D_3 = 1.25$ | 0 | 0 | 31 | 5 | 0 | 0 | 12 | 10 | 9 |
| $D_4 = 2.5$ | 0 | 10 | 52 | 65 | 0 | 0 | 22 | 40 | 25 |

| Product of Example 8 | Post-emergence Treatment Treated plants | | | | | | | | |
|---|---|---|---|---|---|---|---|---|---|
| Dose in kg/ha | wheat | barley | oats | soya bean | rice | cotton | panic | setaria | digitaria |
| $D_1 = 0.312$ | 10 | 11 | 32 | 100 | 32 | 33 | 100 | 92 | 47 |
| $D_2 = 0.625$ | 40 | 40 | 50 | 100 | 30 | 55 | 100 | 100 | 67 |
| $D_3 = 1.25$ | 32 | 47 | 65 | 100 | 30 | 87 | 100 | 100 | 75 |
| $D_4 = 2.5$ | 47 | 82 | 95 | 100 | 40 | 90 | 100 | 100 | 100 |

EXAMPLE 22

The product of Example 8 is applied in open fields by spraying on cultivated plants (wheat, marrow, barley, bean, soya, sunflower, rape, maize, oats, peas, tomato) and undesirable weeds or unwanted plants (goosefoot, amarant, nightshade, dog's mercury, milkweed, bindweed, groundsel, setaria), either at the pre-emergence of the plants immediately after sowing, or at the post-emergence of the plants 15 days after sowing. The doses of product applied are 2.5 or 5 kg/ha.

The results are recorded 7, 14 and 100 days after the treatment (J+7; J+14; J+100). These results are recorded in the Table V. The figures in the table indicate, in the case of the cultivated plants, the vegetative energy of the plants of the plots treated in relation to that of the plants of untreated control plots and, in the case of the undesirable weeks, the percentage of destruction of the plants in the treated plots, this percentage being evaluated by taking as reference plants of untreated control plots.

For a cultivated plant, the FIG. 100 signifies that the vegetative energy of the plant is the same in the treated plots and in the control plots and the FIG. 0 signifies that the plant is entirely destroyed in the treated plots.

For a weed, the FIG. 0 signifies that the state of the plant is the same in the treated plots and the control plots and the FIG. 100 indicates that the plant is entirely destroyed in the treated plots.

EXAMPLE 23

The product of Example 8 is applied by spraying on crops of autumn wheat of the Lutin variety, at different stages of the crop (pre-emergence, 3 leaves, tillering, end of tillering). The doses of product applied are 0.625 or 1.25 kg/ha.

20, 22, 35, 65 and 100 Days after the treatment according to the case (see Table VI for this subject), the effect of treatment is examined on the one hand on the cultivated plant (wheat), and on the other hand in unwanted weeds (veronica or speedwell, meadow-grass, foxtail, chickweed, shepherd's purse).

In no case has any phytotoxicity to wheat been recorded. In Table VI are tabulated the results relative to the rate of destruction of the unwanted weeds. The FIG. 0 corresponds to an undamaged plant, the FIG. 100 to a completely destroyed plant.

What is claimed is:
1. Pyrimidine compounds of the formula:

TABLE VI

| Stage of the crop | Dose kg/ha | Date of Recording | Percentage of destruction of the Plants Product of Example 8 | | | | Shepherd's Purse |
|---|---|---|---|---|---|---|---|
| | | | Unwanted Weeds | | | | |
| | | | Speedwell | Meadow-grass | Foxtail | Chickweed | |
| Pre-emergence | 1.25 | J + 35 | 86 | — | 47 | 100 | — |
| | | J + 65 | 100 | 80 | 52 | 100 | — |
| | | J + 100 | 98 | 88 | 62 | 100 | 100 |
| 3 Leaves | 0.625 | J + 22 | 86 | 41 | 63 | 78 | 80 |
| | | J + 35 | 91 | — | 70 | 70 | 100 |
| | 1.25 | J + 22 | 91 | 100 | 70 | 100 | 100 |
| | | J + 35 | 98 | — | 82 | 100 | 100 |
| Tillering | 1.25 | J + 20 | 85 | 70 | — | 80 | 90 |
| End of Tillering | 1.25 | J + 22 | 80 | — | — | 80 | 90 |

TABLE V

Product of Example 8

| Dose kg/ha | Date of Recording | Cultivated Plant/Vegetative Energy | | | | | | | | | | |
|---|---|---|---|---|---|---|---|---|---|---|---|---|
| | | Wheat | Marrow | Barley | Bean | Soya | Sunflower | Rape | Maize | Oats | Peas | Tomatoes |
| | | Pre-emergence | | | | | | | | | | |
| 2.5 | J + 14 | 100 | 90 | 100 | — | 90 | 80 | 100 | 100 | 100 | 100 | 80 |
| | J + 100 | 0 | 0 | 0 | — | 0 | 20 | 0 | 100 | 0 | 0 | 0 |
| 5 | J + 14 | 70 | 50 | 20 | 90 | 0 | 30 | 0 | 90 | — | 70 | 100 |
| | J + 100 | 0 | 0 | 0 | 0 | 0 | 0 | 0 | 100 | — | 0 | 0 |
| | | Post-emergence | | | | | | | | | | |
| 2.5 | J + 7 | 50 | 20 | 70 | 60 | 0 | 10 | 10 | 60 | 50 | 50 | 40 |
| | J + 14 | 80 | 0 | 60 | 100 | 0 | 30 | 30 | 80 | 70 | 50 | 50 |
| | J + 100 | 60 | 0 | 0 | 0 | 0 | 0 | 0 | 100 | 0 | 0 | 0 |
| 5 | J + 7 | 50 | 10 | 50 | — | 0 | 0 | 0 | 50 | 40 | 0 | 35 |
| | J + 14 | 80 | 5 | 60 | 0 | 0 | 0 | 0 | 100 | 60 | 0 | 15 |
| | J + 100 | 0 | 0 | 0 | 0 | 0 | 0 | 0 | 100 | 0 | 0 | 0 |

| Dose kg/ha | Date of Recording | Wild Plants/ Percentage of Destruction | | | | | | | |
|---|---|---|---|---|---|---|---|---|---|
| | | Goosefoot | Amarant | Nightshade | Dog's Mercury | Milkweed | Bindweed | Groundsel | Setaria |
| | | Pre-emergence | | | | | | | |
| 2.5 | J + 14 | 100 | 100 | 100 | 100 | 100 | 20 | 100 | — |
| | J + 100 | 80 | 100 | 100 | 100 | 100 | 20 | 100 | 30 |
| 5 | J + 14 | 90 | 100 | 100 | 100 | 100 | 80 | 100 | — |
| | J + 100 | 100 | 100 | 100 | 100 | 100 | 100 | 100 | 100 |
| | | Post-emergence | | | | | | | |
| 2.5 | J + 7 | 100 | 100 | 100 | 100 | 100 | 10 | 100 | — |
| | J + 14 | 100 | 100 | 100 | 100 | 100 | 30 | 100 | — |
| | J + 100 | 100 | 100 | 100 | 100 | 100 | 50 | 100 | 60 |
| 5 | J + 7 | 100 | 100 | 100 | 100 | 100 | — | 100 | — |
| | J + 14 | 100 | 100 | 100 | 100 | 100 | — | 100 | — |
| | J + 100 | 100 | 100 | 100 | 100 | 100 | — | 100 | — |

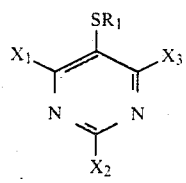 (I)

in which $R_1$ is alkyl having 1 to 5 carbon atoms, $X_1$ is chlorine or bromine, $X_2$ is

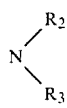

in which $R_2$ is hydrogen or alkyl having 1 to 5 carbon atoms, and $R_3$ is hydrogen, alkyl having 1 to 5 carbon atoms or

R wherein R is hydrogen or alkyl having 1 to 5 carbon atoms, and $X_3$ is

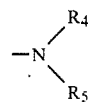

in which $R_4$ is hydrogen and $R_5$ is hydrogen or

R wherein R is as defined above, or their salts with mineral or organic acids.

2. Pyrimidine compounds according to claim 1 in which $X_1$ is chlorine.

3. Pyrimidine compounds according to claim 2 in which $X_3$ is $NH_2$ or

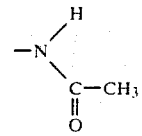

and $X_2$ is methylamino, ethylamino, isopropylamino, amino, or diethylamino.

4. Pyrimidine compounds according to claim 1 in which $X_3$ is

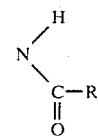

and R is hydrogen or alkyl having 1 to 5 carbon atoms.

5. The compound 2,4-diamino-6-chloro-5-methylthio-pyrimidine.

6. The compound 4-amino-6-chloro-2-ethylamino-5-methylthio-pyrimidine.

7. The compound 6-chloro-2,4-diamino-5-ethylthio-pyrimidine.

8. The compound 6-chloro-2,4-diamino-5-butylthio-pyrimidine.

9. The compound 4-amino-6-chloro-2-diethylamino-5-methylthio-pyrimidine.

10. The compound 2-methylamino-4-amino-6-chloro-5-methylthio-pyrimidine.

11. The compound 4-acetylamino-2-diethylamino-6-chloro-5-methylthio-pyrimidine.

12. Herbicidal compositions which contain inert additives and, as active ingredient, a herbicidally effective amount of at least one compound as defined in claims 1, 2, 3 or 4.

13. Herbicidal compositions according to claim 12 in which the compound included as active ingredient is 2-diethylamino-4-acetylamino-6-chloro-5-methylthio-pyrimidine.

14. Herbicidal compositions according to claim 12 in which the compound included as active ingredient is 2,4-diamino-6-chloro-5-methylthio-pyrimidine.

15. The process for destroying undesirable plants in crops of wheat, barley, rice or maize which comprises applying to said plants or their seeds a herbicidally effective amount of at least one compound as defined in claim 1, 2, 3, or 4.

16. The process according to claim 15 wherein the amount of said compound applied to said plants or their seeds is from 150 g/ha to 2,500 g/ha.

* * * * *